(12) United States Patent
Chin

(10) Patent No.: US 6,694,160 B2
(45) Date of Patent: Feb. 17, 2004

(54) PULSE OXIMETER SENSOR WITH WIDENED METAL STRIP

(75) Inventor: Rodney Chin, Oakland, CA (US)

(73) Assignee: Mallinckrodt Inc., Hazelwood, MO (US)

(*) Notice: Subject to any disclaimer, the term of this patent is extended or adjusted under 35 U.S.C. 154(b) by 0 days.

(21) Appl. No.: 09/998,820

(22) Filed: Nov. 15, 2001

(65) Prior Publication Data

US 2002/0038082 A1 Mar. 28, 2002

Related U.S. Application Data

(63) Continuation of application No. 09/447,455, filed on Nov. 22, 1999.

(51) Int. Cl.[7] .................................................. A61B 5/00
(52) U.S. Cl. ....................................... 600/344; 600/323
(58) Field of Search ................................. 600/309–310, 600/322–324, 344, 340

(56) References Cited

U.S. PATENT DOCUMENTS

| 4,825,872 | A |   | 5/1989  | Tan et al.      |         |
|-----------|---|---|---------|-----------------|---------|
| 4,865,038 | A |   | 9/1989  | Rich et al.     |         |
| 4,964,408 | A |   | 10/1990 | Hink et al.     |         |
| 5,054,488 | A |   | 10/1991 | Muz             |         |
| 5,094,240 | A |   | 3/1992  | Muz             |         |
| 5,209,230 | A |   | 5/1993  | Swedlow et al.  |         |
| 5,237,994 | A |   | 8/1993  | Goldberger      |         |
| 5,246,003 | A |   | 9/1993  | DeLonzor        |         |
| 5,520,177 | A |   | 5/1996  | Ogawa et al.    |         |
| 5,632,273 | A | * | 5/1997  | Suzuki          | 600/310 |
| 5,797,841 | A |   | 8/1998  | Delonzor et al. |         |
| 5,830,136 | A |   | 11/1998 | Delonzor et al. |         |
| 6,112,107 | A | * | 8/2000  | Hannula         | 600/310 |
| 6,208,884 | B1| * | 3/2001  | Kumar et al.    | 600/409 |

FOREIGN PATENT DOCUMENTS

EP          0538631        4/1993

OTHER PUBLICATIONS

US 4,928,691, 5/1990, Nicolson et al. (withdrawn)

* cited by examiner

Primary Examiner—Max F. Hindenburg
Assistant Examiner—Matthew Kremer
(74) Attorney, Agent, or Firm—Townsend and Townsend and Crew LLP

(57) ABSTRACT

A pulse oximeter sensor having an opaque, metalized layer to shield from ambient light. The metalized layer surrounds the area of the light detector. In one embodiment, the sensor has a transparent portion, with the opaque, metalized layer covering only the portions around the light detector and other areas, such as a strip extending between the light detector and the emitter. In a preferred embodiment, the opaque, metalized layer is a strip which has a widened portion in the area around the light detector.

23 Claims, 1 Drawing Sheet

PULSE OXIMETER SENSOR WITH WIDENED METAL STRIP

The present application is a continuation of U.S. patent application Ser. No. 09/447,455 to Rodney Chin, filed Nov. 22, 1999, which is incorporated by reference herein.

BACKGROUND OF THE INVENTION

The present invention relates to pulse oximeter sensors, and in particular to techniques for shielding against ambient light and preventing delamination of flexible, disposable sensors.

A type of pulse oximeter sensor that is commonly used is a flexible, disposable sensor. It typically has multiple layers, with white layers on the outside visible to the user. The white gives the image of cleanliness and sterility, and also is opaque to certain wavelengths of light over the range of the photodetector's sensitivity. An example of a sensor referring to a white opaque layer is set forth in U.S. Pat. No. 4,865,038.

A number of these sensors include metalized layers which can be either a conductive shield or a shield from ambient light. See, for example, U.S. Pat. Nos. 4,928,691; 5,246,003; 5,094,240; 5,054,488; and 4,964,408. U.S. Pat. No. 4,928,691 refers to the use of a red layer to avoid ambient light.

Ambient light can interfere with the operation of a pulse oximeter, especially under the bright lights of surgery or in outdoor, daylight conditions. While the use of a metal layer has been effective to shield from such ambient light, there is also a competing desire to have transparency in order to observe how a sensor is attached. In addition, the introduction of additional layers into the sensor is susceptible to sensor failure by delamination.

Accordingly, it would be desirable to have a sensor which would shield against ambient light, be resistant to delamination and have some transparency.

SUMMARY OF THE INVENTION

The present invention provides a pulse oximeter sensor having an opaque, metalized layer to shield from ambient light. The metalized layer surrounds the area of the light detector. In one embodiment, the sensor has a transparent portion, with the opaque, metalized layer covering only the portions around the light detector and other areas, such as a strip extending between the light detector and the emitter. In a preferred embodiment, the opaque, metalized layer is a strip which has a widened portion in the area around the light detector.

The widened portion of the metalized layer, in conjunction with widened portions that match on adjacent layers, resists delamination stresses.

In another aspect of the invention, the wires connecting to the emitter take an angular path, preferably crossing over from one side of the detector, across a center line between the emitter and detector, to an opposite side of the emitter. This angular path, as opposed to a straight path, disperses stresses caused by the wires, further inhibiting delamination or separation of the layers of the sensor.

In a preferred embodiment, the widened area of the metalized and adjacent layers has a semi-circular profile around the photodetector.

For a further understanding of the nature and advantages of the invention, reference should be made to the following description taken in conjunction with the accompanying drawing.

DESCRIPTION OF THE SPECIFIC EMBODIMENT

Figure 1:
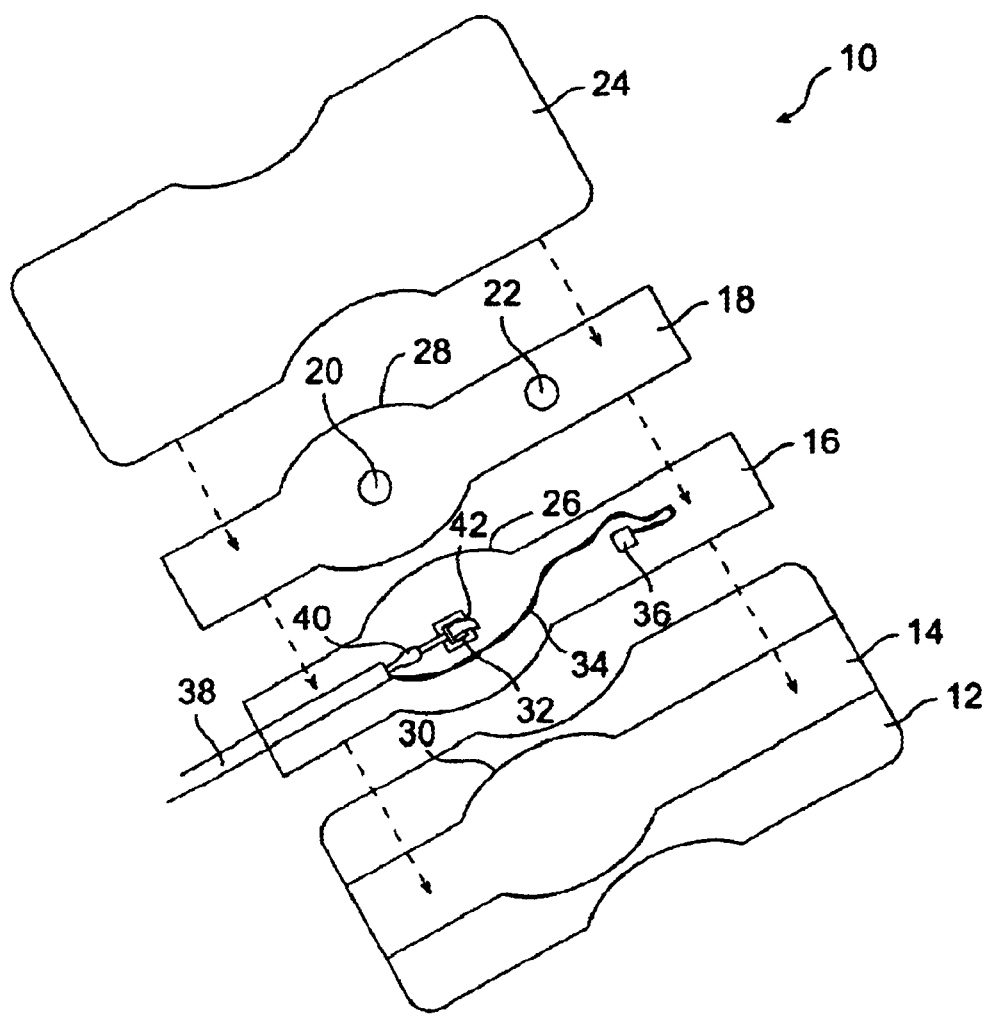
FIG. 1 is an exploded view of a sensor according to the present invention showing the different layers.

FIG. 1 illustrates a sensor 10 according to the invention. The sensor includes a transparent layer 12 which is wider than a white layer 14 mounted on top of it. On top of white layer 14, is mounted a correspondingly-shaped metalized layer 16. On Metalized layer 16 is mounted another white layer 18 having holes 20 and 22 allowing light to pass from/to the emitter and detector. The emitter and detector are mounted on metalized layer 16. Adhesives may be used between layers for mounting. Layer 24 is an adhesive layer disposed on layer 18.

As can be seen, metalized layer 16 includes a widened region defined by a curved perimeter 26. Similar widened regions 28 and 30 are found on white strips 18 and 14, respectively. This widened area surrounds the photodetector 32. Such a widened area prevents ambient light from reaching the photodetector and disturbing its readings. At the same time, by only widening a portion of the strip, other areas of transparent layer 12 allow viewing of the patient when the sensor is attached. This allows, for example, an examination of how tightly the sensor is secured to the patient by looking through transparent layer 12.

Widened area 26 and corresponding widened areas 28 and 30 also resist delamination. As opposed to a straight line strip, these areas are curved such that when the sensor is wrapped around a user's finger or other appendage, the stresses are dispersed rather than being focused on a line. Accordingly, it has been found that this design resists delamination and has fewer failures than a straight strip.

Another stress that can result in delamination is the stress induced by the wires 34 which connect to the emitter or light emitting diode (LED) 36. The present invention reduces the stresses by providing an angular path of wires 34 between cable 38 and photo emitter or LEDs 36. In prior devices, the wires were laid out in a straight line, which was found to contribute to delamination. The angular path where the wires start out beside photodetector 32 and cross the center line between the photodetector and emitter, then above emitter 36 reduces the stresses.

In addition, the wires circle around and attach to photo emitter 36 from the backside, as in previous devices. Also, as in previous devices, photodetector 32, which attached to a coaxial cable 40 inside cable 38, is mounted closer to cable 38 so that the coaxial cable extends onto less of the sensor.

Preferably, metalized layer 16 is a layer of aluminized mylar having a thickness of less than 1 mm. The curved area 26 preferably extends for at least three-quarters of an inch, more preferably slightly more than one inch along the length of strip 16. It preferably extends outward from the straight edge of strip 16 by at least one-eighth of an inch, more preferably approximately one-quarter inch.

FIG. 1 also shows a Faraday shield 42 which wraps around photodetector 32. It is shown partially open in FIG. 1. The Faraday shield is preferably a piece of copper which is solid metal, except for a mesh portion directly above photodetector 32. In one embodiment, part of Faraday shield 42 attaches directly to metal layer 16.

As will be understood by those of skill in the art, the present invention may be embodied in other specific forms without departing from the essential characteristics thereof.

For example, the widened area could be any shape, not just semi-circular. It could be more of an oval shape, square, trapezoidal, etc. Additionally, the metalized layer need not extend the entire length of the sensor, but could simply be in the area around the photodetector, or around the photodetector and photo emitter. Additionally, wires 34 could take any other angular path between the emitter and detector. Also, the strips themselves could be other shapes, with the transparent strip 12 in particular having other patterns for the portion which is viewable. Parts (layers) may have translucent layered components as well as transparent layered components. Layer 16 could be a metalized translucent layer. Layer 12 can be transparent. Layer 18 can be reflective white layer. Layer 24 is not used in a preferred embodiment. Layer 24 can be added if delamination is a problem. In one embodiment there are adhesive layers between each of layers 12, 14 16, and 18.

Accordingly, the foregoing description is intended to be illustrative, but not limiting, of the scope of the invention which is set forth in the following claims.

What is claimed is:

1. A pulse oximeter sensor comprising:

a flexible, transparent substrate;

an opaque layer mounted above said transparent substrate, said opaque layer covering only a portion of said transparent substrate;

a light emitter mounted directly on top of a first side of said opaque layer to emit light away from said opaque layer;

wires mounted on said opaque layer that couple said light emitter to a cable;

a light detector mounted directly on top of said first side of said opaque layer, said opaque layer being a strip extending at least from said emitter to said detector, said strip having a first portion adjacent said detector that is wider than a second portion of said strip adjacent to said emitter; and a non-transparent layer mounted over said light emitter and said detector, said non-transparent layer having holes over said light emitter and detector, wherein said wires cross a center line between said light emitter and said light detector.

2. A pulse oximeter sensor comprising:

a flexible, transparent substrate;

an opaque layer mounted above said transparent substrate, said opaque layer covering only a portion of said transparent substrate;

a light emitter mounted directly on top of a first side of said opaque layer to emit light away from said opaque layer;

wires mounted on said opaque layer that couple said light emitter to a cable;

a light detector mounted directly on top said first side of said opaque layer, said opaque layer being a strip extending at least from said emitter to said detector, said strip having a first portion adjacent said detector that is wider than a second portion of said strip adjacent to said emitter;

a non-transparent layer mounted over said light emitter and said detector, said non-transparent layer having holes over said light emitter and detector; and a second flexible, non-transparent layer mounted between said transparent substrate and said opaque layer.

3. A pulse oximeter sensor comprising:

a flexible, transparent substrate;

an opaque layer mounted above said transparent substrate, said opaque layer covering only a portion of said transparent substrate;

a light emitter mounted directly on top of a first side of said opaque layer to emit light away from said opaque layer;

wires mounted on said opaque layer that couple said light emitter to a cable;

a light detector mounted directly on top of said first side of said opaque layer, said opaque layer being a strip extending at least from said emitter to said detector, said strip having a first portion adjacent said detector that is wider than a second portion of said strip adjacent to said emitter; and a non-transparent layer mounted over said light emitter and said detector, said non-transparent layer having holes over said light emitter and detector;

wherein said wider portion of said strip has a curved perimeter.

4. A pulse oximeter sensor comprising:

an opaque layer having a first portion that is wider than a second portion of said opaque layer, said first portion having a curved perimeter;

a light emitter mounted on top of a first side of said opaque layer adjacent said second portion of said opaque layer to emit light away from said opaque layer;

a light detector mounted on top of said first side of said opaque layer adjacent said first portion of said opaque layer;

said opaque layer extending at least from said emitter to said detector; and a non-transparent strip mounted over said light emitter and said detector, said non-transparent strip having holes over said light emitter and detector, said non-transparent strip having a wider portion matching the shape of said first portion of said opaque layer.

5. The pulse oximeter sensor of claim 4 further comprising a cable extending into said sensor, said detector being mounted closer to said cable than said emitter, and further comprising wires from said cable connecting to said emitter, said wires crossing over a line between said emitter and said detector in a region between said emitter and said detector.

6. The pulse oximeter sensor of claim 4 further comprising a second non-transparent layer mounted under said opaque layer having a wider portion matching the shape of said first portion of said opaque layer.

7. The sensor of claim 4 wherein said curved perimeter extends along at least three quarters of an inch on both sides of said strip adjacent said detector, and extends outward at least an eighth of an inch from said strip at a maximum point of extension.

8. A pulse oximeter sensor comprising:

a flexible, transparent substrate;

a first non-transparent layer mounted over said transparent substrate and only covering a portion of said transparent substrate;

an opaque, metalized layer directly mounted on said first non-transparent layer, said metallized layer covering only said first non-transparent layer;

a light emitter mounted on a first side of said metalized layer to emit light away from said metalized layer;

a light detector mounted on said first side of said metalized layer;

wires mounted on said metalized layer that couple said light emitter to a cable, said wires crossing a center line between said light emitter and said light detector; and a second non-transparent layer mounted over said light emitter and said detector, said second non-transparent layer having holes over said light emitter and detector.

9. The pulse oximeter sensor of claim 8 wherein said metalized layer comprises a strip extending at least from said emitter to said detector, said strip having a wider portion adjacent said detector.

10. The sensor of claim 9 wherein said wider portion of said strip has a curved perimeter.

11. The sensor of claim 10 wherein said curved perimeter extends along at least three quarters of an inch on both sides of said strip adjacent said detector, and extends outward at least an eight of an inch from said strip at a maximum point of extension.

12. The sensor of claim 10 wherein said second non-transparent layer comprises a strip having a wider portion matching said wider portion of said metalized layer.

13. A pulse oximeter sensor comprising:

a flexible, transparent substrate;

an opaque layer mounted on a first side of said transparent substrate, said opaque layer covering only a portion of said transparent substrate;

a light emitter mounted directly on top of a first side of said opaque layer to emit light away from said opaque layer;

a light detector mounted directly on top of said first side of said opaque layer;

a non-transparent layer mounted over said light emitter and said detector, said non-transparent layer having holes over said light emitter and detector, and an adhesive layer disposed on said non-transparent layer and a portion of said transparent layer not covered by said opaque layer and said non-transparent layer, wherein said opaque layer comprises a strip extending at least from said emitter to said detector, said strip having a wider portion adjacent to said detector than adjacent to said emitter, and said wider portion of said strip has a curved perimeter.

14. The sensor of claim 13 wherein said curved perimeter extends along at least three quarters of an inch on both sides of said strip adjacent said detector, and extends outward at least an eighth of an inch from said strip at a maximum point of extension.

15. The sensor of claim 13 wherein said non-transparent layer comprises a strip having a wider portion matching said wider portion of said opaque layer.

16. A pulse oximeter sensor comprising:

a flexile, transparent substrate;

an opaqune layer mounted on a first side of said transparent substrate, said opaque layer covering only a portion of said transparent substrate;

a light emitter mounted directly an top of a first side of said opaque layer to emit light away from said opaque layer;

a light detector mounted directly on top of said first side of said opaque layer, said opaque layer being a strip extending at least from said emitter to said detector, said strip having a first portion adjacent said detector that is wider than a second portion of said strip adjacent to said emitter;

a non-transparent layer mounted over said light emitter and said detector, said non-transparent layer having holes over said light emitter and detector;

an adhesive layer disposed on said non-transparent layer and a portion of said transparent layer not covered by said opaque layer and said non-transparent layer;

a cable extending into said sensor, said detector being mounted closer to said cable than said emitter, and wires from said cable connecting to said emitter, said wires crossing over a line between said emitter and said detector in a region between said emitter and said detector.

17. A pulse oximeter sensor comprising:

a flexible, transparent substrate;

a first flexible, non-transparent layer mounted on said transparent substrate;

an opaque layer mounted on a first side of said first non-transparent layer, said opaque layer covering only a portion of said transparent substrate;

a light emitter directly mounted on top of a first side of said opaque layer to emit light away from said opaque layer;

a light detector directly mounted on top of said first side of said opaque layer, said opaque layer being a strip extending at least from said emitter to said detector, said strip having a first portion adjacent said detector that is wider than a second portion of said strip adjacent to said emitter, said first portion of said strip having a curved perimeter;

a second non-transparent layer mounted over said light emitter and said detector, said second non-transparent layer having holes over said light emitter and detector; and an adhesive layer disposed on said second non-transparent layer and a portion of said transparent layer not covered by said opaque layer and said first non-transparent layer.

18. The sensor of claim 17 wherein said curved perimeter extends along at least three quarters inch on both sides of said strip adjacent said detector, and extends outward at least an eight of an inch from said strip at a maximum point of extension.

19. The sensor of claim 17 further comprising a cable extending into said sensor, said detector being mounted closer to said cable than said emitter, and further comprising wires from said cable connecting to said emitter, said wires crossing over a line between said emitter and said detector in a region between said emitter and said detector.

20. The sensor of claim 17, further comprising a Faraday shield at least partially surrounding said detector, said Faraday shield being connected to said opaque layer.

21. A pulse oximeter sensor comprising:

an opaque layer having a first portion that is wider than a second portion of said opaque layer, said first portion having a curved perimeter;

a light emitter directly mounted on top of a first side of said opaque layer adjacent said second portion to emit light away from said opaque layer;

a light detector directly mounted on top of said first side of said opaque layer adjacent said first portion of said opaque layer;

said opaque layer extending at least from said emitter to said detector, a non-transparent strip mounted over said light emitter and said detector, said non-transparent strip having holes over said light emitter and detector, said non-transparent strip having a wider portion matching the shape of said first portion of said opaque layer;

an adhesive layer disposed on said non-transparent strip;

a cable extending into said sensor, said detector being mounted closer to said cable than said emitter; and wires from said cable connecting to said emitter, said wires crossing over a line between said emitter and said detector in a region between said emitter and said detector.

22. A pulse oximeter sensor comprising:

a flexible, transparent substrate;

a first non-transparent layer mounted over said transparent substrate and only covering a portion of said transparent substrates;

an opaque layer directly mounted on said first non-transparent layer, said opaque layer covering only said first non-transparent layer;

a light emitter mounted on a first side of said opaque layer to emit light any from said opaque layer;

a light detector mounted on said first side of said opaque layer;

a second non-transparent layer mounted over said light emitter and said detector, said second non-transparent layer having holes over said light emitter and detector; and an adhesive layer disposed on said second non-transparent layer and a portion of said transparent layer not covered by said opaque layer and said second non-transparent layer, wherein said opaque layer comprises a strip extending at least from said emitter to said detector, said strip having a wider portion adjacent said detector than adjacent said emitter.

23. A pulse oximeter sensor comprising:

a flexible, transparent substrate;

a first flexible, non-transparent layer mounted on said transparent substrate and covering only a portion of said transparent substrate;

an opaque layer mounted directly on said first non-transparent layer;

a light emitter mounted on a first side of said opaque layer to emit light away from said opaque layer;

a light detector mounted on said first side of said opaque layer, said opaque layer being a strip extending at least from said emitter to said detector, said strip having a wider portion adjacent said detector than adjacent emitter said wider portion of said strip having a curved perimeter;

a second non-transparent layer mounted over said light emitter and said detector, said second non-transparent layer having holes over said light emitter and detector; and an adhesive layer disposed on said second non-transparent layer and a portion of said transparent layer not covered by said opaque layer and said first non-transparent layer.

* * * * *